United States Patent
Yoon et al.

(10) Patent No.: US 8,507,554 B2
(45) Date of Patent: Aug. 13, 2013

(54) QUORUM SENSING ANTAGONIST AND METHOD OF REDUCING A BACTERIAL CONTAMINATION USING THE QUORUM SENSING ANTAGONIST

(75) Inventors: Je-Yong Yoon, Seoul (KR); Cheol-Jin Kim, Seoul (KR); Jae-Eun Kim, Daegu (KR); Hyung-Yeon Park, Incheon (KR)

(73) Assignee: Seoul National University Industry Foundation, Seoul (KR)

( * ) Notice: Subject to any disclaimer, the term of this patent is extended or adjusted under 35 U.S.C. 154(b) by 649 days.

(21) Appl. No.: 12/067,731

(22) PCT Filed: May 3, 2007

(86) PCT No.: PCT/KR2007/002169
§ 371 (c)(1),
(2), (4) Date: Aug. 4, 2010

(87) PCT Pub. No.: WO2008/069374
PCT Pub. Date: Jun. 12, 2008

(65) Prior Publication Data
US 2010/0292261 A1    Nov. 18, 2010

(30) Foreign Application Priority Data
Dec. 4, 2006 (KR) .......................... 10-2006-0121650

(51) Int. Cl.
*A61K 31/34* (2006.01)
*A61K 31/215* (2006.01)

(52) U.S. Cl.
USPC ............ 514/471; 514/472; 514/473; 514/507

(58) Field of Classification Search
USPC .................................. 514/471, 472, 473, 507
See application file for complete search history.

(56) References Cited

U.S. PATENT DOCUMENTS
6,555,356 B2 * 4/2003 Kjelleberg et al. ........... 435/244

OTHER PUBLICATIONS

Al-Bataineh et al., "XPS characterization of the surface immobilization of antibacterial furanones", Surface Science, vol. 600, No. 4, pp. 952-962.*

* cited by examiner

*Primary Examiner* — Kevin E Weddington
(74) *Attorney, Agent, or Firm* — Lee, Hong, Degerman, Kang & Waimey

(57) ABSTRACT

In the quorum sensing antagonist blocking the communication in bacteria, the method for preventing biofilm formation using this quorum sensing antagonist and the method for reducing the bacterial contamination, the quorum sensing antagonist contains the homoserine lactone moiety and sulfanylethanoyl group, and has a similar chemical structure to that of the autoinducer which is produced by bacteria as a signal, whereby the quorum sensing antagonist can inhibit the formation of biofilm and reduce the bacterial contamination as well.

20 Claims, 8 Drawing Sheets

QUORUM SENSING ANTAGONIST AND METHOD OF REDUCING A BACTERIAL CONTAMINATION USING THE QUORUM SENSING ANTAGONIST

CROSS-REFERENCE TO RELATED APPLICATIONS

This application is the National Stage filing under 35 U.S.C. 371 of International Application No. PCT/KR2007/002169, filed on May 3, 2007, which claims the benefit of earlier filing date and right of priority to Korean Application No. 10-2006-0121650, filed on Dec. 4, 2006.

FIELD OF THE INVENTION

This invention relates generally to quorum sensing antagonists and methods for preventing a biofilm formation and reducing a bacterial contamination using the quorum sensing antagonist.

BACKGROUND OF THE INVENTION

Controlling the growth of pathogenic bacteria is one of the biggest issues in the field of biological chemistry. Two representative pathogenic bacteria in plants and animals are *Agrobacterium tumefaciens*(*A. tumefaciens*) and *Pseudomonas aeruginosa*(*P. aeruginosa*). *A. tumefaciens* is known to be the cause of Crown Gall disease. Crown gall, a disease of roots and stems, occurs in over 140 species of dicotyledon. *P. aeruginosa* makes biofilms. A biofilm is a slimy layer composed of microorganisms attached to a surface by extracellular polymeric substances (EPS) secreted by the cells during metabolism. *P. aeruginosa* in biofilms has the capability to protect themselves from attacks by other agents such as antibiotics.

Understanding quorum sensing (QS) mechanism is important to solve the problems such as diseases and biofilm formation which get accomplished by bacterial QS. Bacteria communicate with each other by a mechanism known as QS. QS is a term to describe the phenomenon that a single cell senses the cell density. Bacteria release signaling molecules or autoinducers (AI) out of the cell. Once bacteria reach a high cell density, a high concentration of AI accumulates in the surrounding medium. AI docks with a receptor protein in a cell and AI-receptor protein complex regulates various gene expressions concerning the production of virulence factors, biofilms and infection of plant or animal, depending on a cell density.

Therefore, it is necessary to develop the antagonizing agents that can interfere with the normal QS regulation for controlling the undesired bacterial activities, such as virulence factor production by pathogenic bacteria or biofilm formation by environmental microorganisms.

Moreover, the development of new antagonist blocking QS regulation of various bacteria is demanded.

DETAILED DESCRIPTION OF THE INVENTION

One object of this invention is to provide QS antagonist inhibiting gene expression and blocking cell to cell communication of various bacteria. Another object of this invention is to provide a method blocking biofilm formation using this QS antagonists. Still another object of this invention is to provide a method blocking bacterial contamination using this QS antagonists.

QS antagonists to achieve the object of this invention described above are compounds according to the following general formula 1 or 2.

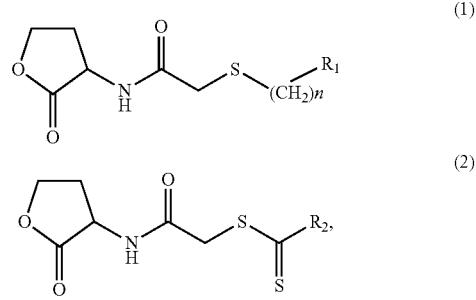

Where n is an integer from 0 to 10, R1 is hydrogen, hetero aromatic containing nitrogen, or carboxyl carboxyalkylthio group which has a carbon number from 1 to 10, R2 is aromatic or carboxyl carboxyalkylthio group which has a carbon number from 1 to 10. In a blocking method of biofilm formation according to another object of the present invention, biofilm formation is blocked by contacting QS antagonists to bacteria according to formula 1 or 2.

According to an exemplary embodiment of the present invention, the QS antagonists may contact bacteria to use acylhomoserine lactone as an autoinducer. For example, the QS antagonists may contact Gram-negative bacteria.

In a method of reducing a bacterial contamination using the quorum sensing antagonist according to still another object of the present invention, the bacterial contamination is blocked by contacting the QS antagonists expressed by formula 1 or 2 to an object. According to an exemplary embodiment, contact between QS antagonist and the object may be performed by spray, dipping, or brush method using solution including the quorum sensing antagonist.

Since QS antagonists described above have very similar chemical structure to that of autoinducer or signal that bacteria use to communicate each other, they can interfere with the gene expression by controlling bacterial communication. In addition, they can effectively block propagation, virulence factor production and biofilm formation by bacteria.

BRIEF DESCRIPTION OF THE DRAWINGS

Bioassay for new antagonists. The antagonists show a smaller color change than the reference

DETAILED DESCRIPTION OF THE INVENTION

Figure 1:
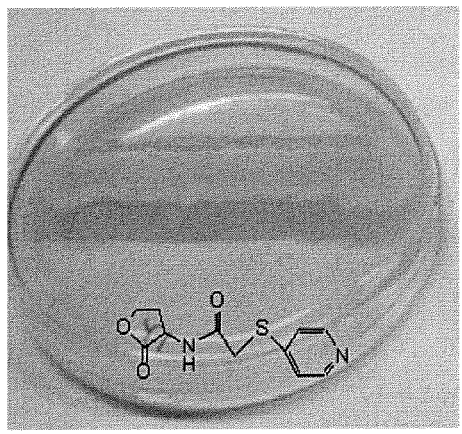
FIGS. 1 to 8 are photographs illustrating color changes in the experimental results for the activities of the control (or reference example 1) and QS antagonists synthesized according to exemplary embodiments 1 to 7.
Figure 2:
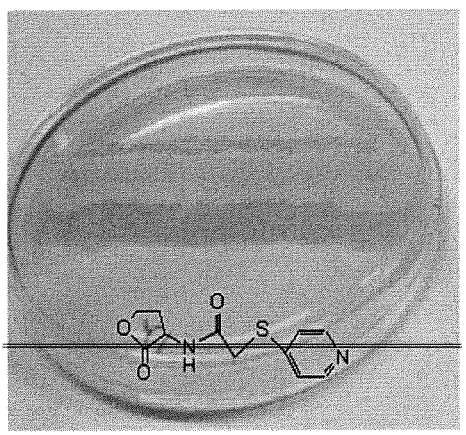
Figure 3:
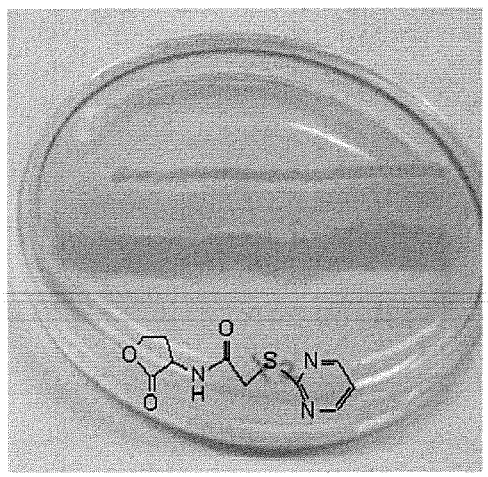
Figure 4:
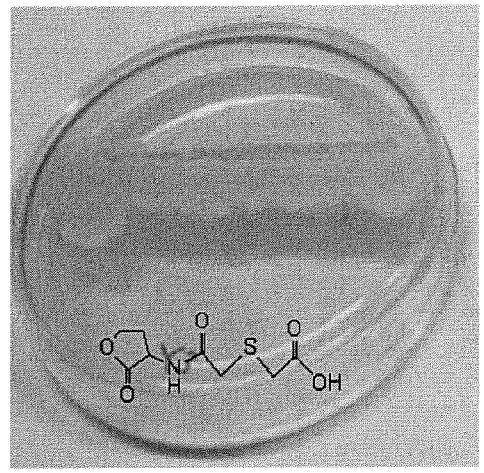
Figure 5:
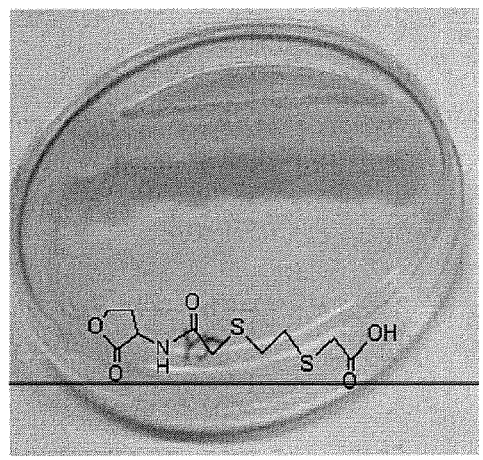
Figure 6:
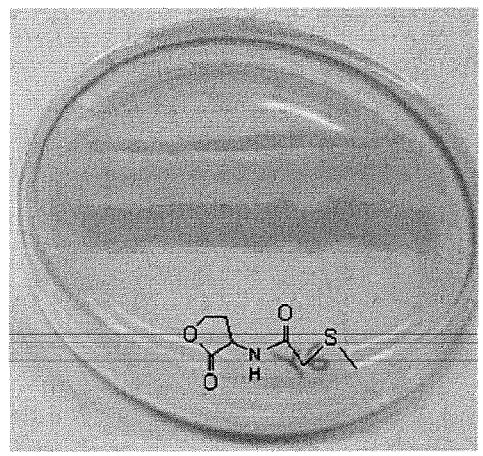
Figure 7:
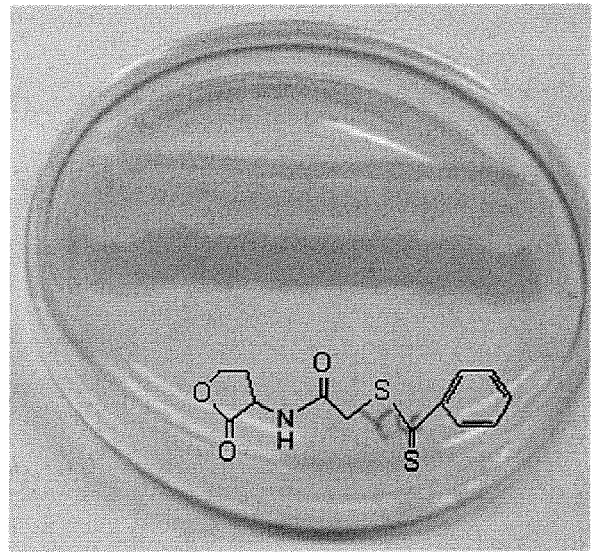
Figure 8:
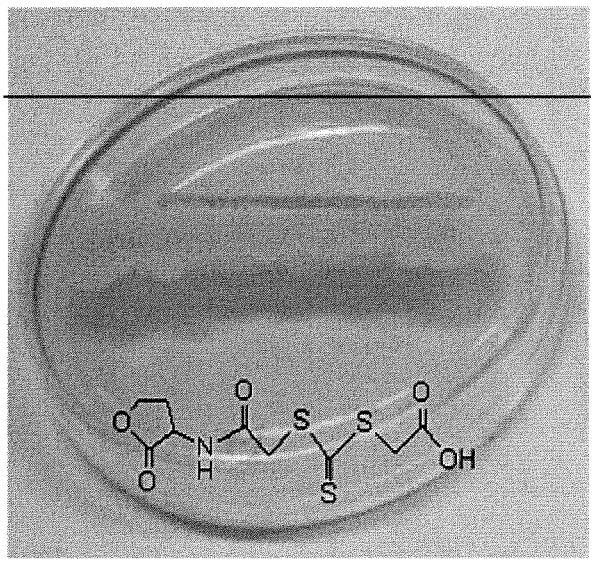

Quorum sensing antagonist of this invention and methods for preventing a biofilm formation using quorum sensing antagonist are explained in detail hereinafter.

QS antagonists according to the present invention may have structures as shown in the following formula 1 or 2.

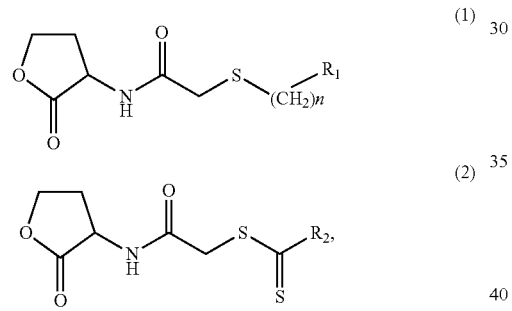

Where n defines an integer from 0 to 10, R1 is hydrogen, hetero aromatic containing nitrogen, or carboxyl carboxyalkylthio group which has a carbon number from 1 to 10, R2 is aromatic or carboxyl carboxyalkylthio group which has a carbon number from 1 to 10.

QS antagonists having structures as described in formula 1 may contain homoserine lactone group and sulfanyl ethanoyl group. This quorum sensing antagonist according to the present invention has the similar chemical structure to that of N-acylhomoserine lactone which is used by bacteria as an autoinducer, and has the ability to block cell-to-cell communication.

According to the example, QS antagonists described as in formula 1 may have schematic structure as illustrated in formulae 3 to 7.

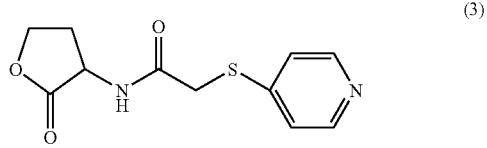 [SMILES: O=C(CSc1ccncc1)NC1CCOC1=O]

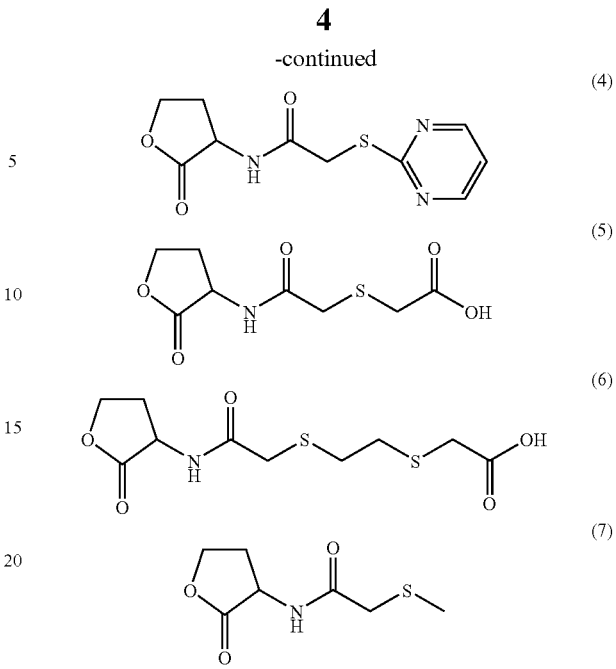

QS antagonists described in formula 2 may have schematic structure as shown in formulae 8 to 9.

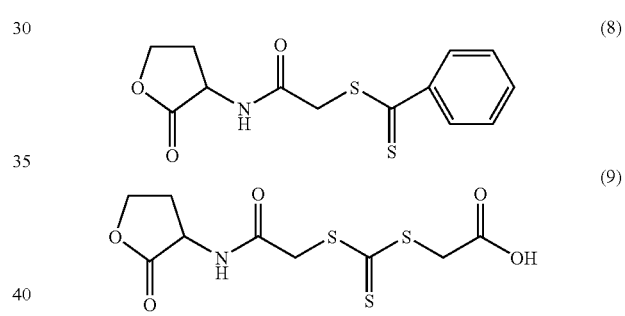

QS antagonists described as in formula 1 or 2 may be synthesized by replacing the hydrogen at the amine group of homoserine lactone with sulfanyl ethanoyl group.

For example, the quorum sensing antagonist shown as in formula 3 was replaced by the hydrogen of the amino group of homoserine lactone with the pyridinylsulfanylacetyl group in response to reaction between homoserine lactone and [(2-pyridine-4-ylthio) acetic acid. In addition, the quorum sensing antagonist shown in formula 8 was replaced by the hydrogen of the amino group of homoserine lactone with the acetyl group of 2-(phenylcarbonothioylthio) acetic acid according to the reaction between homoserine lactone and 2-(phenylcarbonothioylthio) acetic acid.

According to the exemplary embodiment, the quorum sensing antagonist may be 2-(phenylcarbonothioylthio) acetyl homoserine lactone indicated in Formula 8. 2-(phenylcarbonothioylthio) acetyl homoserine lactone may be stably docked to the receptor protein of Gram-negative bacteria such as *Agrobacterium tumefaciens* because it has the lower bonding energy than the autoinductor.

In addition, 2-(phenylcarbonothioylthio) acetyl homoserine lactone may also act as the quorum sensing antagonist to inhibit QS of many types of Gram-negative bacteria. For example, the 2-(phenylcarbonothioylthio) acetyl homoserine lactone may act as the quorum sensing antagonist to block QS of the Gram-negative bacteria such as *Vibrio* harveyi, *Agrobacterium tumefaciens* and *E. coli* DH5α co-transformed by two compatible plasmids, pJN105L and pSC11.

The quorum sensing antagonist according to the present invention has the similar chemical structure to that of acyl-homoserine lactone which is used by bacteria as an autoinducer, or the signaling material. We may take N-(3-hydroxybutanoyl) homoserine lactone, N-(3-(oxohexanoyl) homoserine lactone, N-(3-oxooctanoyl) homoserine lactone, N-(3-oxododecanoyl) homoserine lactone, N-(butanoyl) homoserine lactone, N-(hexanoyl) homoserine lactone, and N-(octanoyl) homoserine lactone as the examples of the acyl-homoserine lactone above. The 2-(phenylcarbonothioylthio) acetyl homoserine lactone competes with the autoinductor described above to dock to the receptor protein of Gram-negative bacteria, thus inhibiting the gene expression by the autoinductor.

The quorum sensing antagonist according to the instant invention may act as a quorum sensing antagonist to block QS of bacteria which uses the above mentioned acylhomoserine lactone as an autoinducer. We may take the Gram-negative bacteria as the bacteria using acylhomoserine lactone as an autoinductor. We may take *Vibrio* harveyi, *Agrobacterium tumefaciens, Pseudomonas aeruginosa, Escherichia coli, Aerononas hydrophila, Burkholderia cepacia, Chromobacterium violaceum, Enterobacter agglomerans, Erwinia stewarti, Nitrosomas europea, Photobacterium fischeri, Pseudomonas aureofaciens, Rhizobium leguminosarum, Serratia liquefaciens, Vibrio Fischeri*, etc as the examples of the above mentioned Gram-negative bacteria. The quorum sensing antagonist according to the present invention may effectively block the gene expression, the breakup of disease, and the formation of biofilm by inhibiting cell-to-cell communication.

Now, description is made as to how to prevent the biofilm formation and how to reduce the contamination by bacteria using the quorum sensing antagonist according to the following invention.

According to the exemplary embodiment, biofilm formation on the surface may be inhibited by contacting the quorum sensing antagonist with the bacteria. Biofilm is a structured community of microbial cells enclosed in a self-produced polymeric matrix and adherent to an inert or living surface. The above mentioned biofilm causes diseases by staying in the organs of human body. As the quorum sensing antagonist has the structure as described in formula 1 or formula 2, it inhibits the communication between bacteria, thus inhibiting the biofilm formation and reducing the contamination by bacteria.

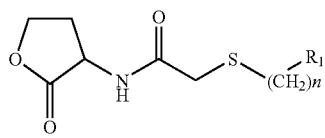

(1)

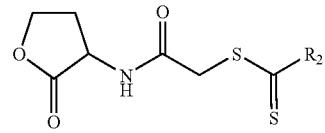

(2)

In the formulae 1 and 2, the n defines an integer from 0 to 10 and the R1 indicates hydrogen, carboxyl group, nitrogen-containing hetero aromatic hydrocarbon group, or carboxyalkylthio group having a carbon number from 1 to 10. R2 means either aromatic hydrocarbon group or carboxyalkylthio group with a carbon number from 1 to 10. According to the exemplary embodiment, the quorum sensing antagonist may block the biofilm formed by the bacteria which use the acylhomoserine lactone as the autoinductor. We may take the Gram-negative bacteria such as *Vibrio harveyi, Agrobacterium tumefaciens, Pseudomonas aeruginosa, Escherichia coli*, etc as examples of bacteria which form the biofilm above.

According to the exemplary embodiment, an exemplary object may be a medical device or a home appliance. It should be noted that the exemplary object may comprise any structure that can prevent the biofilm formation or bacterial contamination. In addition, the contact of quorum sensing antagonist with bacteria does not require any special method but may be easily done, for example, by using the solvent like water as a medium.

According to the exemplary embodiment, the bacterial contamination may be reduced by contacting the quorum sensing antagonist with the object. For example, the solution of the above mentioned quorum sensing antagonist may be applied to the above object by using spray, dipping, or brush. However there is no limitation of method to contact. As described above, the quorum sensing antagonist according to the present invention can inhibit the communication between bacteria and thus prevent an attack of a disease and the formation of biofilm. Accordingly, the quorum sensing antagonist according to the instant invention can effectively inhibit the formation of biofilm and reduce the contamination by bacteria by applying itself on the device or a tool in which the biofilm is easily formed by contacting water.

Now, the present invention will be described in detail with reference to the exemplary embodiments and comparative embodiments. However the exemplary embodiment below is just for demonstration of the invention and its experimental example is not limited thereto, but subject to change or modification depending on the experimental circumstances.

Preparation of the Quorum Sensing Antagonist

The quorum sensing antagonist described as formula 1 or 2 was prepared by method according to reaction schemes 1 to 4.

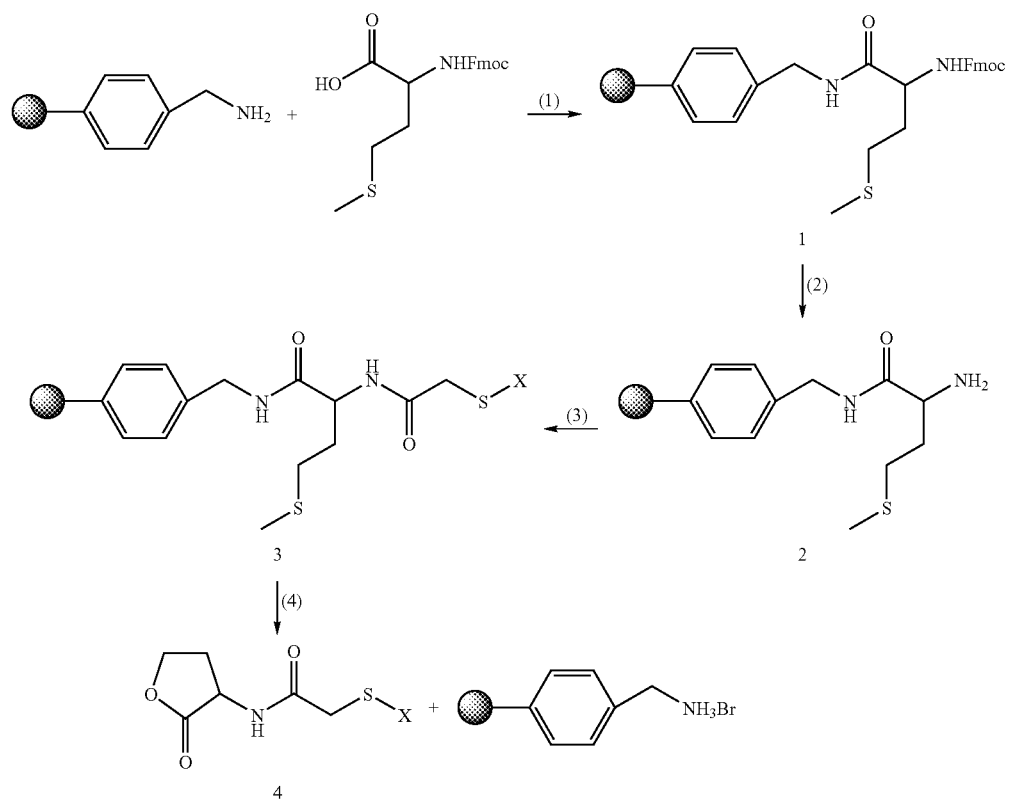

Examplary Embodiment 1

10 g (22 mmol) of an aminomethyl polystyrene resin (AM PS, 200-400 mesh, 2.2 mmol/g, Beadtech Inc., South Korea) was swollen in 100 mL of N-methyl-2-pyrrolidone (NMP) in a 3-neck flask (250 mL). To introduce a methionine residue onto the resin, N-Fmoc-methionine (14.86 g, 40 mmol), 1-hydroxybenzotriazole (HOBt, 5.33 g, 40 mmol), diisopropyl ethylamine (DIEA, 5.17 g, 40 mmol), and benzotriazol-1-yl-oxy-tris(dimethylamino)phosphonium hexafluorophosphate (BOP, 17.69 g, 40 mmol), acting as coupling agents, were added to the flask. The solution was then stirred at room temperature for 12 hours, and the completion of the reaction was determined using a Ninhydrin color test. After filtering the N-Fmoc methionine-coupled resin, the resin was washed two or three times with NMP, methylene chloride (MC), and methanol, followed by drying in vacuo (mass increase: 8.17 g, yield: 99.82%). The resin (Resultant 1 described above) was confirmed to contain an amide bond as a result of the coupling reaction based on the FT-IR spectrum, which showed amide peaks at 1718 and 1670 cm$^{-1}$.

To remove the Fmoc group from the Resultant 1, N-Fmoc methionine-mediated resin, the resin (11 g) was then treated twice with piperidine/dimethylformamide (DMF) (20%, v/v) at room temperature for 1 hour each time. Thereafter, the resin was filtered, washed two or three times with DMF, MC, and methanol, and dried in vacuo to measure final mass of Resultant 2 (7.13 g). A Ninhydrin test indicated that the solution contained an amine group, although the amide band disappeared from the FT-IR spectrum (1718 cm$^{-1}$).

The Resultant 2, Fmoc-removed resin (500 mg) was then swollen in NMP (15 mL) in each of the eleven filtered reactors (Libra tube RT-20M, Beadtech Inc., South Korea). The resin was reacted with the N-(alkylsulfanylethanoyl)-L-HSL derivatives, N-(fluoroalkanoyl)-L-HSL derivatives, N-(fluorosulfonyl)-L-HSL, or 2,2 dimethyl butanoyl-L-HSL (2.8 mmol) in the presence of HOBt (378.28 mg, 2.8 mmol), BOP (1238.44 mg, 2.8 mmol), and DIEA (361.9 mg, 2.8 mmol). The reaction was carried out by reaction scheme 3 at room temperature for 12 hours, then the reaction mixture was filtered and washed with NMP, MC, and methanol, followed by drying in vacuo. At last, Resultant 3 was obtained. The reaction yield was investigated based on the mass increase, which ranged from 90 to 94%.

To prepare a series of homoserine lactones, the Resultant 3 resin was treated with BrCN (860 mg, 8 mmol) and trifluoroacetic acid (TFA, 5%) in chloroform/water (10 mL/5 mL) in each of the filtered reactors. The homoserine lactone derivative products were then cleaved from the beads twice for 12 hours using a chemical cleavage method. Thereafter, the resin was filtered and washed two or three times with chloroform, then the cleavage and washing solution were collected in a round-bottom flask (100 mL) and the chloroform layer was separated. The collected solution was extracted several times with CHCl3 and brine, then the final chloroform solution was evaporated. At last, final resultant 4 was obtained.

The structure of resultant 4 compound was finally confirmed using such techniques as NMR and GC/MS. The NMR spectrometer was operated using CDCl3 solvent at 400 MHz. Chemical shift (δ) was observed in 8.52 (d, J=7.24 hz, 2H, Ar—H), 8.29 (s, 1H, NH), 7.34 (d, J=6.53 hz, 2H, Ar—H), 4.46-4.24 (m, 3H, CH-Lac), 3.82 (s, 2H, CH2), 2.46-2.42 (m, 1H, CH-Lac), and 2.19-2.15 (m, 1H, CH-Lac).

Mass Spectrum peak (252.2940) of C11H12N2O3S was observed in 252.2939 using high resolution mass spectroscopy.

Therefore, it was finally confirmed that the resultant compound (4) was N-(2-oxo-tetrahydrofuran-3-yl)-2-(pyridin-4-ylthio)acetamide as described in Formula 3 below.

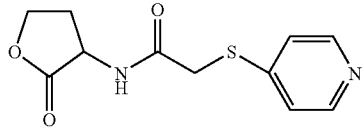

(3)

Examplary Embodiment 2

Final resultant 4 was produced by the same method as that of the first exemplary embodiment to get product except that 2-(pyrimidin-2-ylthio)acetic acid was used instead of 2-(pyridin-4-ylthio)acetic acid.

The structure of resultant compound was finally confirmed using such techniques as NMR and GC/MS. The NMR spectrometer was operated using CDCl3 solvent at 400 MHz. Chemical shift (δ) was observed in δ=8.61 (d, J=5.4 Hz, 1H, CH), 8.60 (d, J=5.0 Hz, 1H, CH), 8.29 (s, 1H, NH), 7.09 (t, 1H, CH), 4.46-4.24 (m, 3H, CH-Lac), 3.83 (s, 2H, CH2), 2.42-2.45 (m, 1H, CH-Lac), 2.07-2.00 (m, 1H, CH-Lac). Mass Spectrum peak (253.2818) of C11H12N2O3S was observed in 253.2817 using high resolution mass spectroscopy.

Therefore, it was finally confirmed that the resultant compound (4) was N-(2-oxo-tetrahydrofuran-3-yl)-2-(pyridin-4-ylthio)acetamide as described in Formula 4 below.

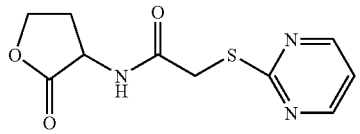

(4)

Examplary Embodiment 3

Final resultant 4 was produced by the same method as that of the first exemplary embodiment to get product except that 2,2'-thiodiacetic acid was used instead of 2-(pyridin-4-ylthio) acetic acid.

The structure of resultant compound was finally confirmed using such techniques as NMR and GC/MS. The NMR spectrometer was operated using CDCl3 solvent at 400 MHz. Chemical shift (δ) was observed in δ=12.34 (s, H, OH), 8.30 (s, 1H, NH), 4.46-4.24 (m, 3H, CH-Lac), 3.37 (s, 2H, CH2), 3.32 (s, 2H, CH2), 2.43-2.45 (m, 1H, CH-Lac) and 2.20-2.17 (m, 1H, CH-Lac).

Mass Spectrum peak (233.2451) of C11H12N2O3S was observed in 233.2451 using high resolution mass spectroscopy.

Therefore, it was finally confirmed that the resultant compound (4) was 2-(2-oxo-2-(2-oxo-tetrahydrofuran-3-ylamino)ethylthio)acetic acid as described in Formula 5 below.

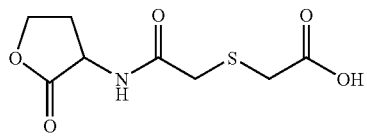

(5)

Examplary Embodiment 4

Final resultant (4) was produced by the same method as that of the first exemplary embodiment to get product except that 2,2'-(ethane-1,2-diylbis(sulfanediyl))diacetic acid was used instead of 2-(pyridin-4-ylthio)acetic acid.

The structure of resultant compound was finally confirmed using such techniques as NMR and GC/MS. The NMR spectrometer was operated using CDCl3 solvent at 400 MHz. Chemical shift (δ) was observed in δ=12.33 (s, H, OH), 8.34 (s, 1H, NH), 4.41-4.24 (m, 3H, CH-Lac), 3.39 (s, 2H, CH2), 3.32 (s, 2H, CH2), 2.83 (s, 4H, CH2), 2.46-2.42 (m, 1H, CH-Lac)및 2.19-2.16 (m, 1H, CH-Lac).

Mass Spectrum peak (293.3648) of C11H12N2O3S was observed in 293.3649 using high resolution mass spectroscopy.

Therefore, it was finally confirmed that the resultant compound (4) was 2-(2-(2-oxo-2-(2-oxo-tetrahydrofuran-3-ylamino) ethylthio)ethylthio)acetic acid as described in Formula 6 below.

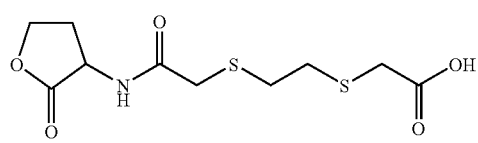

(6)

Examplary Embodiment 5

Final resultant (4) was produced by the same method as that of the first exemplary embodiment to get product except that 2-(methylthio)acetic acid was used instead of 2-(pyridin-4-ylthio)acetic acid.

The structure of resultant compound was finally confirmed using such techniques as NMR and GC/MS. The NMR spectrometer was operated using CDCl3 solvent at 400 MHz. Chemical shift (δ) was observed in δ=8.18 (s, 1H, NH), 4.44-4.24 (m, 3H, CH-Lac), 3.33 (s, 2H, CH2), 2.47-2.42 (m, 1H, CH-Lac), 2.21-2.17 (m, 1H, CH-Lac) and 2.10 (s, 3H, CH3).

Mass Spectrum peak (189.2353) of C11H12N2O3S was observed in 189.2353 using high resolution mass spectroscopy.

Therefore, it was finally confirmed that the resultant compound (4) was 2-(methylthio)-N-(2-oxo-tetrahydrofuran-3-yl)acetamide as described in Formula 7 below.

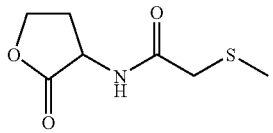

(7)

Examplary Embodiment 6

Final resultant (4) was produced by the same method as that of the first exemplary embodiment to get product except that 2-(phenylcarbonothioylthio)acetic acid was used instead of 2-(pyridin-4-ylthio)acetic acid.

The structure of resultant compound was finally confirmed using such techniques as NMR and GC/MS. The NMR spectrometer was operated using CDCl3 solvent at 400 MHz. Chemical shift (δ) was observed in δ=8.03 (s, 1H, NH), 7.45-7.41 (m, 3H, Ar—H), 7.3 (d, J=5.48 hz 2H, Ar—H), 4.52-4.21 (m, 3H, CH-Lac), 3.78 (s, 2H, CH2), 2.46-2.39 (m, 1H, CH-Lac) and 2.22-2.17 (m, 1H, CH-Lac).

Mass Spectrum peak (295.3832) of C11H12N2O3S was observed in 295.3831 using high resolution mass spectroscopy.

Therefore, it was finally confirmed that the resultant compound (4) was 2-(phenylcarbonothioylthio)acetyl homoserine lactone as described in Formula 8 below.

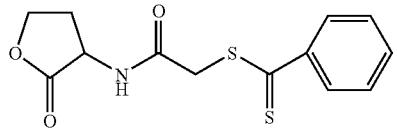

(8)

Examplary Embodiment 7

Final resultant (4) was produced by the same method as that of the first exemplary embodiment to get product except that 2,2'-thiocarbonylbis(sulfanediyl)diacetic acid was used instead of 2-(pyridin-4-ylthio)acetic acid.

The structure of resultant compound was finally confirmed using such techniques as NMR and GC/MS. The NMR spectrometer was operated using CDCl3 solvent at 400 MHz. Chemical shift (δ) was observed in δ=12.3:3 (s, H, OH), 8.19 (s, 1H, NH), 4.42-4.25 (m, 3H, CH-Lac), 3.80 (s, 2H, CH2), 3.73 (s, 2H, CH2), 2.47-2.42 (m, 1H, CH-Lac) and 2.17-2.14 (m, 1H, CH-Lac).

Mass Spectrum peak (309.3881) of C11H12N2O3S was observed in 309.3881 using high resolution mass spectroscopy.

Therefore, it was finally confirmed that the resultant compound (4) was 2-{((2-oxo-2-(2-oxo-tetrahydrofuran-3-ylamino)ethylthio)carbonothioylthio}acetic acid as described in Formula 9 below.

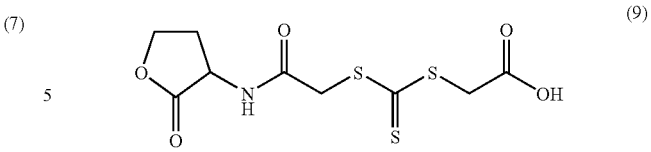

(9)

Bioassay of QS Antagonism

Tests were conducted to confirm whether new homoserinelactone derivatives produced as results of exemplary embodiments 1-7 can block bacterial QS as a quorum sensing antagonist.

*Agrobacterium tumefaciens* A136(pTiA136, pCF218, pCF372) and *Agrobacterium tumefaciens* KYC6 were used as the indicating microorganisms.

*Agrobacterium tumefaciens* A136(pTiA136, pCF218, pCF372) are bacteria mutated to produce β-galactosidase by expressing the lac gene when exposed to HSL. Moreover, *Agrobacterium tumefaciens* KYC6 are bacteria mutated to overproduce AHL.

The tests were conducted to confirm if *Agrobacterium tumefaciens* A136 produce β-galactosidase by exposing themselves to acylhomoserinelactone using 5-bromo-4-chloro-3-indolyl-β-D-galactopyranoside (X-gal) which gives off a green or blue color when degraded by the β-galactosidase produced.

To put it concretely, the *Agrobacterium tumefaciens* KYC6 type-culture strain was cultured overnight in an LB (Luria-Bertani) broth at 30° C. 10 μL of the KYC6 strain and 100 μL of the homoserinelactone derivatives produced as results of exemplary embodiments 1-7 were inoculated into 5 mL of an LB broth and cultured for 24 hours at 30° C. C. Moreover, *Agrobacterium tumefaciens* A136 strain was also cultured overnight at 30° C. in an LB broth containing 50 μg/mL of spectinomycin and 4.5 μg/mL of tetracycline. Moreover, instead of homoserinelactone derivatives, distilled water was used for the comparative example 1.

To examine if new inventions are quorum sensing antagonists, 16 μL of an X-gal (50 mg/mL)/DMF solution and 50 μL of distilled water were spread on an LB agar. The A136 strain was then streaked onto the middle of the LB agar plate using a platinum loop. Thereafter, the KYC6 strains cultured with the homoserinelactone derivatives were streaked 1-2 cm away from the A136 line, and the LB agar plates incubated for two days until a green or blue color was found in the distilled water was used instead of homoserinelactone derivatives as a comparative example 1 at 30° C. The experimental result was shown in from FIG. 1 to FIG. 8.

FIGS. 1~8 are photographs which show color change of the LB agar plate cultured for the experiments using the distilled water according to the comparative example 1 and the synthesized antagonists according to exemplary embodiments 1~8.

In the experiment using the distilled water of the comparative example 1, the color of the medium plate, which is located *Agrobacterium tumefaciens* A136, was clearly dark blue. In contrast, in the experimental plate using quorum sensing antagonists according to the present invention, there was shown a smaller degree of color change or no color change at all at a partial area which contained *Agrobacterium tumefaciens A*136. Consequently, we can identify that quorum sensing antagonists according to the present invention repress gene expression by competing with AI's docking to receptor protein of *Agrobacterium tumefaciens* KYC6 and block *Agrobacterium tumefaciens* A136 to produce galactosidase. Therefore, it was proven that homoserine lactone derivatives according to the instant invention exhibited outstanding antagonism as quorum sensing antagonists Evaluation of Binding Energy Molecular docking work between the receptor protein of *Agrobacterium tumefaciens* (gram negative) and 2-(phenylcarbonotiolthio) homoserine lactone molecule as represented by the exemplary embodiment 8 was performed to identify binding energy thereof.

We used X-ray crystallographic structure which has been previously performed to explain the quorum-sensing transcription factor complexed with autoinducer and DNA of *Agrobacterium tumefaciens* (pdb code=1 L3L).

In order to study active site and interaction of receptor protein of *Agrobacterium tumefaciens* and 2-(phenylcarbonotiolthio) homoserine lactone molecule, we performed molecular modeling studies using SYBYL packages To be more specific, FlexX docking of 2-(phenylcarbonotiolthio) homoserine lactone molecule was performed using the Run-Multiple Ligand option of FlexX. Among several possible poses, the optimal conformational binding pose was selected based on the root-mean-square (RMS) deviation from the reference structure. Furthermore, chemical and physical properties of active site region were characterized using MOLCAD surface program.

Molecular dockings between the receptor and molecule were performed to identify biological activity and structure was sketched and optimized using the Tripos force field until RMS gradient was less than 0.05.

We found that binding mode between AI ligand in the crystal structure and the best-docked structure was almost same and best docking mode of hydrophilic interaction between active site and 2-(phenylcarbonotiolthio) acetyl homoserine lactone molecule without steric hinderance.

Figure 9:
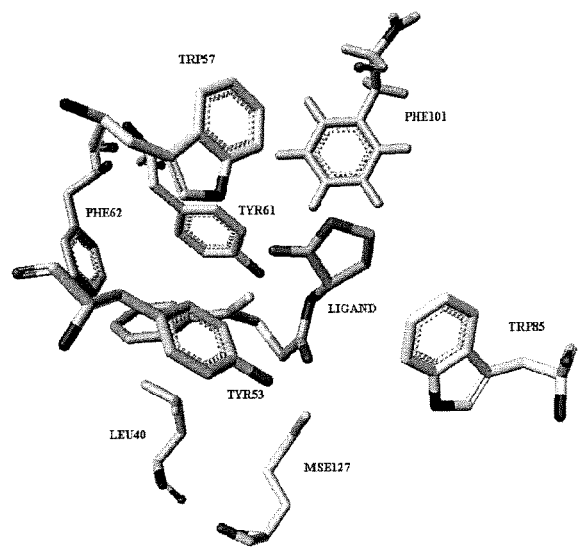
FIG. 9 is a mimetic diagram of 2-(phenylcarbonothioylthio)acetyl homoserine lactone at binding site of the receptor protein of *Agrobacterium tumefaciens*.

The best molecular docking mode between active site of the receptor protein and 2-(phenylcarbonotiolthio) acetyl homoserine lactone molecule was presented in FIG. 9.

In FIG. 9, Ligand represented 2-(phenylcarbonotiolthio) acetyl homoserine lactone, molecules around Ligand were active site residues of receptor protein and hydrogen atoms were removed.

From the best binding pose in FIG. 9, we used FlexX program to study binding energy of the receptor protein of *Agrobacterium tumefaciens* (gram negative) and 2-(phenylcarbonotiolthio) homoserine lactone, a result of which is summarized in Table 1.

TABLE 1

| Ligand | Binding energies (kcal/mol) |
|---|---|
| Autoinducer | −12.78 |
| 2-(phenylcarbonothioylthio) acetyl homoserine lactone | −20.17 |

With reference to Table 1, the binding energy of 2-(phenylcarbonotiolthio) homoserine lactone was found to be less than that of the autoinducer, which suggests that lactone moiety has a better inhibition activity than that of the autoinducer.

Evaluation of Quorum-Sensing Antagonistic Ability of 2-(Phenylcarbonothioylthio) Acetyl Homoserine Lactone Quorum-sensing antagonistic ability of 2-(phenylcarbonothioylthio) acetyl homoserine lactone described in Formula 8 was evaluated. The evaluation was performed using *Vibrio harveyi* BB886, *Agrobacterium tumefaciens* A136(Ti—) (pCF218)(pCF372), *E. coli* DH5α which was co-transformed two compatible plasmids, pJN105L (LasR expression plasmid) and pSC11 (lasI::lacZ fusion reporter plasmid) as reporter strains.

Evaluation of Quorum-Sensing Antagonistic Ability of 2-(Phenylcarbonothioylthio) Acetyl Homoserine Lactone Using *Vibrio Harveyi* BB886

Quorum-sensing antagonistic ability of 2-(phenylcarbonothioylthio) acetyl homoserine lactone as described in Formula 8 was evaluated using *Vibrio harveyi* strain BB886 which responds to the AI-1, i.e., N-(3-hydroxybutanoyl)-1-homoserine lactone (3-OH—C4-HSL) as reporter strain. *Vibrio harveyi* strain BB886 was grown in LBS medium (10 g/L tryptone, 5 g/L yeast extract, 20 g/L NaCl) at 30° C. For the bioluminescence assay, an overnight culture was diluted 100-fold in a sterile AI bioassay (AB) medium (300 mM NaCl, 50 mM MgSO4, 0.2% (w/v) vitamin-free casamino acid, 10 mM potassium phosphate, 1 mM 1-arginine, 1% glycerol; pH 7.5).

No. 1 solution, which was dissolved 3-hydroxybutanoyl homoserine lactone (autoinducer) in chloroform and No. 2, 3, 4 solutions, which were dissolved 3-hydroxybutanoyl homoserine lactone and 2-(phenylcarbonothioylthio) acetyl homoserine lactone in chloroform were prepared. No. 1 solution contained 1 μM of autoinducer. Moreover No. 2, 3, 4 solutions contained 1 μM of autoinducer and various concentrations (1, 5, or 10 μM) of 2-(phenylcarbonothioylthio) acetyl homoserine lactone.

After vaporizing chloroform in 4 test tubes at 30° C. for 2 hours, 4.0 mL of the diluted reporter strain culture was added to No. 1~No. 4 test tubes and incubated at 30° C. Luminescence measurements were performed after 2 hours of incubation using a luminescence meter (Thermo Electron Co.). Bacterial cell density was measured by optical densities at 600 nm (OD600) using a UV spectrophotometer (HP8452A, H.P.). The antagonist activities of 2-(phenylcarbonothioylthio) acetyl homoserine lactone were expressed as a specific luminescence; relative light units/OD600.

Figure 10:
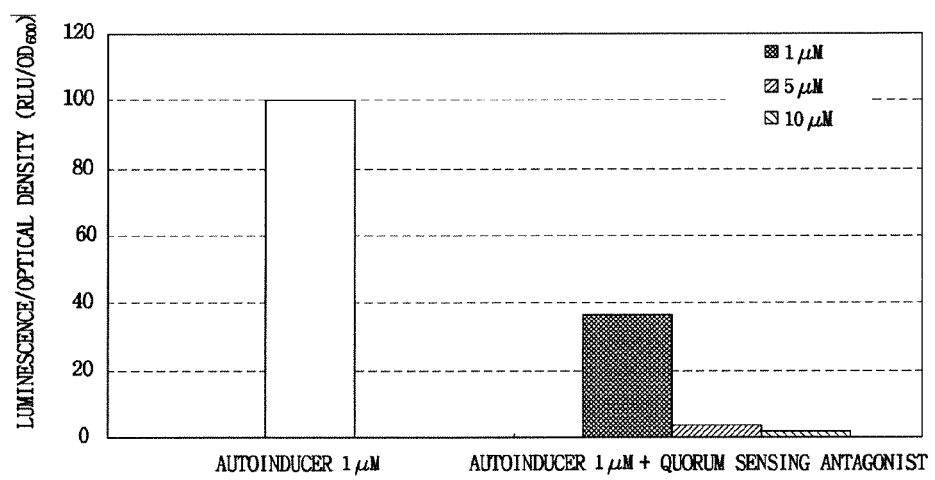
FIG. 10 illustrates experimental results for inhibition efficacy of 2-(phenylcarbonothioylthio)acetyl homoserine lactone against autoinducer of *Vibrio harveyi*.

FIG. 10 is a graph of an evaluation result for antagonist activity using the reporter strain *V. harveyi* BB886 in order to identify 2-(phenylcarbonothioylthio) acetyl homoserine lactone that could compete against AI-1 and repress lux-operon expression. To put it concretely, FIG. 10 illustrates an RLU ratio of *V. harveyi* BB886 grown for 2 hours in the presence of 1 μM autoinducer or 1 μM autoinducer plus 0 μM, 5 μM, 10 μM of 2-(phenylcarbonothioylthio) acetyl homoserine lactone.

As shown in FIG. 10, it was examined that the luminescence intensity per *V. harveyi* was relatively high in a sample containing only 3-hydroxybutanoylhomoserine lactone. This shows a case where the gene expression was activated by the autoinducer, whereby the luminescence intensity per *V. harveyi* was high.

In contrast, the luminescence assays performed on 2-(phenylcarbonothioylthio) acetyl homoserine lactone showed that the intensity of *V. harveyi* luminescence decreased remarkably by increasing the concentration of compound used.

This means that 2-(phenylcarbonothioylthio) acetyl homoserine lactone has eminent quorum-sensing inhibiting ability to suppress *V. harveyi* gene expression.

Evaluation of quorum-sensing antagonistic ability of 2-(phenylcarbonothioylthio) acetyl homoserine lactone using *Agrobacterium tumefaciens* A136 (pTiA136, pCF218, pCF372)

Quorum-sensing antagonistic ability of 2-(phenylcarbonothioylthio) acetyl homoserine lactone as described in Formula 8 was evaluated using *Agrobacterium tumefaciens*

A136(pTiA136, pCF218, pCF372)) which responds to the autoinducer, 3-oxootanoyl homoserine lactone (3-oxo-C8-HSL) as reporter strain.

*A. tumefaciens* A136 (pTiA136, pCF218, and pCF372) was cultured in Luria-Bertani (LB) media with 50 μg/mL spectinomycin and 4.5 μg/mL tetracycline at 30° C. For the bioassay of 2-(phenylcarbonothioylthio) acetyl homoserine lactone, an overnight culture was diluted at 1:100 and incubated up to an optical density of 0.3 at 600 nm (OD600) at 30° C.

No. 1 solution, which was dissolved 3-oxootanoyl homoserine lactone (autoinducer) in chloroform and No. 2 solution, which was dissolved 3-oxootanoyl homoserine lactone and 2-(phenylcarbonothioylthio) acetyl homoserine lactone in chloroform were prepared. No. 1 solution contained 0.5 μM of N-3-oxootanoyl homoserine lactone. No. 2 solution contained 0.5 μM of autoinducer and 5 μM of 2-(phenylcarbonothioylthio) acetyl homoserine lactone.

After vaporizing chloroform in 2 test tubes at 30° C. for 2 hours, 4.0 mL of the diluted reporter strain culture was added to No. 1 and No. 2 test tubes. The solution containing no autoinducer and 2-(phenylcarbonothioylthio) acetyl homoserine lactone as a control experiment was also prepared and incubated at 30° C. for 3 hours.

LacZ quantative analysis for test tubes described above was performed using Tropix-plus kit (Applied Biosystems, USA). Luminescence measurements were performed after 2 hours of incubation using a luminescence meter (Thermo Electron Co.). Bacterial cell density was measured by optical densities at 600 nm (OD600) using a UV spectrophotometer (HP8452A, H. P.). The antagonist activities of 2-(phenylcarbonothioylthio) acetyl homoserine lactone were expressed as a specific luminescence; relative light units/OD600. Luminescence measurements for the culture solution containing no autoinducer and 2-(phenylcarbonothioylthio) acetyl homoserine lactone as a control experiment were performed.

Figure 11:
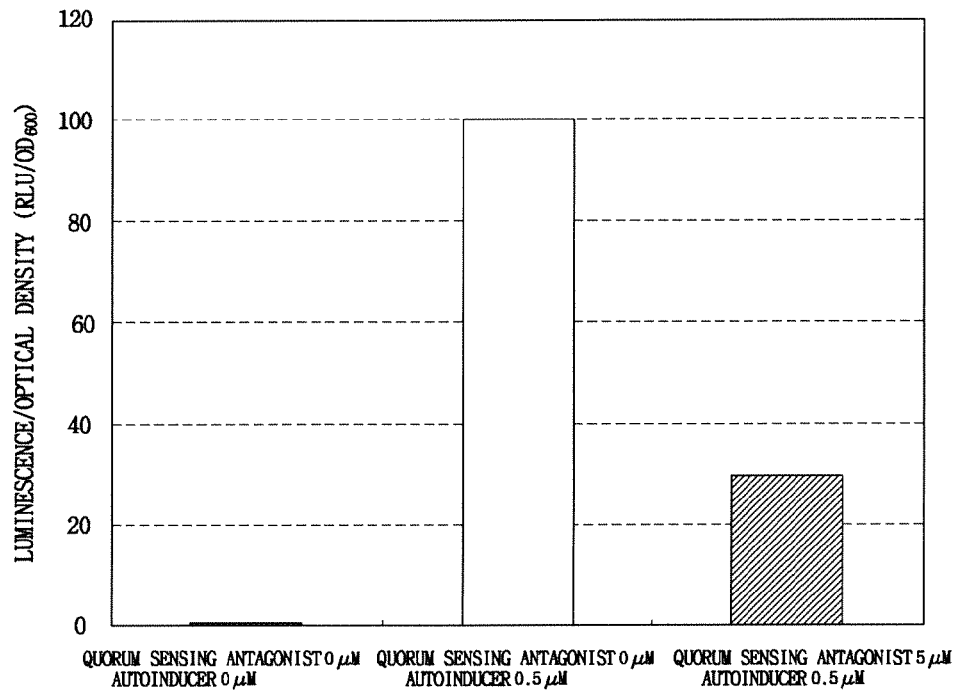
FIG. 11 illustrates experimental results for inhibition efficacy of 2-(phenylcarbonothioylthio)acetyl homoserine lactone against autoinducer of *Agrobacterium tumefaciens*.

FIG. 11 is a graph of an evaluation result for antagonist activity using the reporter strain *A. tumefaciens* A136 (pTiA136, pCF218, and pCF372) in order to identify 2-(phenylcarbonothioylthio) acetyl homoserine lactone that could compete against autoinducer, N-3-oxootanoyl homoserine lactone and repress gene expression. To put it concretely, FIG. 11 illustrates an RLU ratio of *A. tumefaciens* A136 (pTiA136, pCF218, and pCF372) grown for 2 hours in the presence of the culture solution containing no autoinducer and 2-(phenylcarbonothioylthio) acetyl homoserine lactone, or the culture solution containing 0.5 μM autoinducer, or the culture solution containing 0.5 μM autoinducer plus 5 μM of 2-(phenylcarbonothioylthio) acetyl homoserine lactone.

As shown in FIG. 11, in case 2-(phenylcarbonothioylthio) acetyl homoserine lactone was added in test tube containing N-3-oxootanoyl homoserine lactone, it was examined the luminescence intensity per *A. tumefaciens* A136 (pTiA136, pCF218, and pCF372) decreased remarkably.

This means that 2-(phenylcarbonothioylthio) acetyl homoserine lactone has eminent quorum-sensing inhibiting ability to suppress gene expression and cell-cell communication of *A. tumefaciens* A136 (pTiA136, pCF218, and pCF372).

Evaluation of quorum-sensing antagonistic ability of 2-(phenylcarbonothioylthio) acetyl homoserine lactone using *E. coli* DH5α co-transformed by two kinds of plasmid, pJN105L (LasR expression plasmid) and pSC11 (lasI::lacZ fusion reporter plasmid) Quorum-sensing antagonistic ability of 2-(phenylcarbonothioylthio) acetyl homoserine lactone as described in Formula 8 was evaluated using *E. coli* DH5α co-transformed by two kinds of plasmid, pJN105L (LasR expression plasmid) and pSC11 (lasI::lacZ fusion reporter plasmid) which responds to the autoinducer, 3-oxododecanoyl homoserine lactone (3-oxo-C12-HSL) as reporter strain.

Transformant *E. coli* was cultured in Luria-Bertani (LB) broth with 10 μg/mL gentamicin and 50 μg/mL ampicillin at 37° C.

For LacZ bioassay of 2-(phenylcarbonothioylthio) acetyl homoserine lactone, an overnight culture was diluted at 1:100 and incubated up to an optical density of 0.3 at 600 nm (OD600) at 30° C. Then, 0.4% arabinose was added.

No. 1 solution, which was dissolved 3-oxododecanoyl homoserine lactone, 3-oxo-C12-HSL (*Pseudomonas aeruginosa* autoinducer) in chloroform and No. 2, 3, 4 solutions, which were dissolved 3-oxododecanoyl homoserine lactone and 2-(phenylcarbonothioylthio) acetyl homoserine lactone in chloroform were prepared. No. 1 solution contained 1 μM of autoinducer. No. 2, 3, 4 solutions contained 1 μM of autoinducer and various concentrations (1, 2, or 10 μM) of 2-(phenylcarbonothioylthio) acetyl homoserine lactone. After vaporizing chloroform in 4 test tubes at 37° C. for 2 hours, 4.0 mL of the diluted reporter strain culture was added to No. 1~No. 4 test tubes.

The solution containing no autoinducer and 2-(phenylcarbonothioylthio) acetyl homoserine lactone as a control experiment was also prepared and incubated at 37° C. for 3 h.

LacZ Bioassay for test tubes described above was performed using Tropix-plus kit (Applied Biosystems, USA). Luminescence measurements were performed after 2 hours of incubation using a luminescence meter (Thermo Electron Co.). Bacterial cell density was measured by optical densities at 600 nm (OD600) using a UV spectrophotometer (HP8452A, H.P.).

The antagonist activities of 2-(phenylcarbonothioylthio) acetyl homoserine lactone were expressed as a specific luminescence; relative light units/OD600. Luminescence measurements for the culture solution containing no autoinducer and 2-(phenylcarbonothioylthio) acetyl homoserine lactone as a control experiment were performed.

Figure 12:
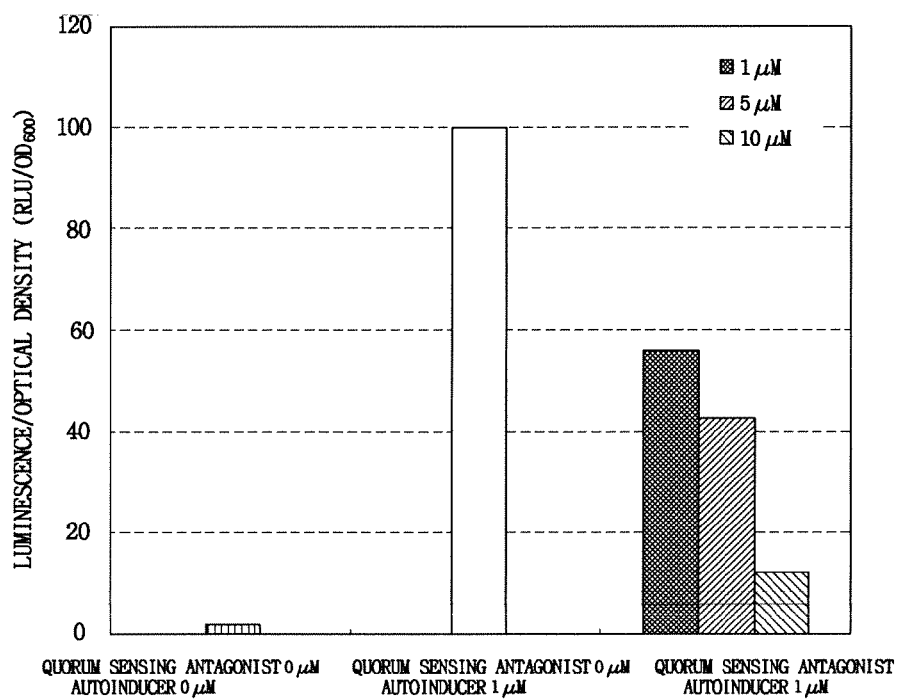
FIG. 12 illustrates experimental results for inhibition efficacy of 2-(phenylcarbonothioylthio)acetyl homoserine lactone against autoinducer of *Pseudomonas aeruginosa*.

FIG. 12 is a graph of an evaluation result for antagonist activity using *E. coli* DH5α co-transformed by two kinds of plasmid, pJN105L (LasR expression plasmid) and pSC11 (lasI::lacZ fusion reporter plasmid) in order to identify 2-(phenylcarbonothioylthio) acetyl homoserine lactone that could compete against autoinducer, N-3-oxododecanoyl homoserine lactone and repress gene expression.

To put it concretely, FIG. 12 illustrates RLU ratio of co-transformed *E. coli* DH5α grown for 2 hours in the presence of the culture solution containing no autoinducer and 2-(phenylcarbonothioylthio) acetyl homoserine lactone, or the culture solution containing 1 μM autoinducer, or the culture solution containing 1 μM autoinducer plus 1 μM, 2 μM, 10 μM of 2-(phenylcarbonothioylthio) acetyl homoserine lactone. As shown in FIG. 12, in case 2-(phenylcarbonothioylthio) acetyl homoserine lactone was added in test tube containing N-3-oxododecanoyl homoserine lactone, it was examined the luminescence intensity per co-transformed *E. coli* DH5α decreased remarkably.

This means that 2-(phenylcarbonothioylthio) acetyl homoserine lactone has eminent quorum-sensing inhibiting ability to suppress gene expression and cell-cell communication of co-transformed *E. coli* DH5α or *Pseudomonas aeruginosa*.

In conclusion, it was examined that 2-(phenylcarbonothioylthio) acetyl homoserine lactone according to the present invention competes with the autoinductor to dock to the receptor protein of *V. harveyi*, *A. tumefaciens* A136

(pTiA136, pCF218, and pCF372), co-transformed *E. coli* DH5α, or *Pseudomonas aeruginosa* and block gene expression. Therefore, it was proven that 2-(phenylcarbonothioylthio) acetyl homoserine lactone of this invention has eminent quorum-sensing inhibiting ability against various bacteria.

Evaluation of Inhibiting Ability Against Biofilm Formation

Inhibiting ability against biofilm formation of quorum-sensing antagonist prepared according to exemplary embodiments 1-7 was evaluated.

Specimen was set in nutrient flask containing 10 μmol/L of quorum-sensing antagonist prepared according to exemplary embodiments 1-7 and *P. aeruginosa* which has strong adhesive character on surface. Numbers of adhesive *P. aeruginosa* on surface were counted after 4 hours. Distilled water was poured into nutrient flask instead of quorum-sensing antagonist as a comparison example 1. Numbers of adhesive *P. aeruginosa* on surface were counted after 4 hours. Moreover, autoinducer, N-3-oxododecanoylhomoserinelactone was filled into nutrient flask instead of quorum-sensing antagonist as a comparative example 2. Numbers of adhesive *P. aeruginosa* on surface were counted after 4 hours. Number of *P. aeruginosa* attached on surface after 4 hours and the percentage where the comparative example 2 was set at 100% are shown in Table 2.

TABLE 2

|  | Numbers of adhesive *P. aeruginosa* [CFU/cm2] | % |
| --- | --- | --- |
| Example 1 | 3.0 × 107 | 40 |
| Example 2 | 3.8 × 107 | 51 |
| Example 3 | 2.5 × 107 | 33 |
| Example 4 | 1.0 × 107 | 13 |
| Example 5 | 2.3 × 107 | 30 |
| Example 6 | 1.5 × 107 | 20 |
| Example 7 | 2.3 × 107 | 30 |
| Comparative example 1 | 7.5 × 107 | 100 |
| Comparative example 2 | 1.4 × 108 | 190 |

As shown in Table 2, the extent of *P. aeruginosa* adhesion in nutrient flask containing QS antagonists prepared according to exemplary embodiments 1-7 was much less than that of *P. aeruginosa* adhesion in nutrient flask containing distilled water and autoinducer prepared in comparative examples 1 and 2.

Specimens were set in nutrient flasks containing compounds according to the first exemplary embodiment 1, comparative examples 1 and 2. Biofilm was grown on the specimens for 48 hours. The specimen were examined using microscope. Furthermore, specimens were set in nutrient flasks containing compounds according to exemplary embodiment 6 and comparative example 2. Biofilm on the specimens was grown for 48 hours. The specimens were examined using a microscope.

Figure 13:
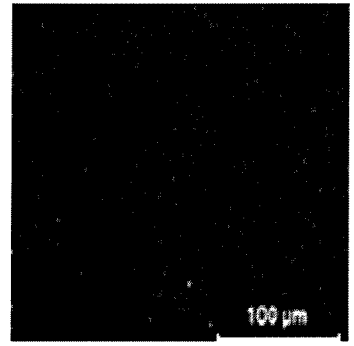
FIG. 13 illustrates Micrographs of *P. aeruginosa* biofilms grown on glass slide in case of using QS antagonist synthesized according to first exemplary embodiment.
Figure 14:
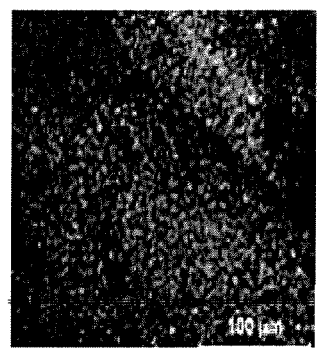
FIG. 14 illustrates Micrographs of *P. aeruginosa* biofilms grown on glass slide in case of using only distilled water according to comparative example 1.
Figure 15:
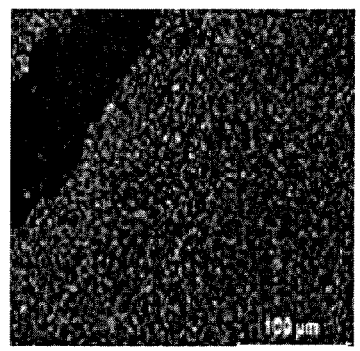
FIG. 15 illustrates Micrographs of *P. aeruginosa* biofilms grown on glass slide in solution of autoinducer according to comparative example 2.
Figure 16:
FIGS. 16-18 illustrate Micrographs of *P. aeruginosa* biofilms grown on glass slide in solution of antagonist synthesized according to exemplary embodiment 6.
Figure 17:
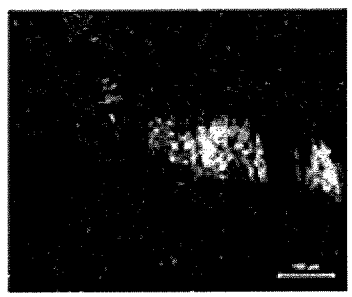
Figure 18:
Figure 19:
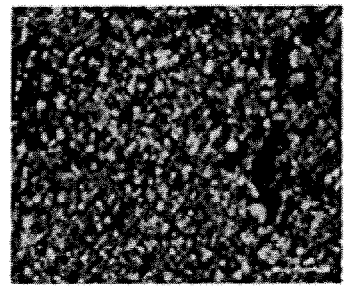
FIGS. 19-21 illustrate Micrographs of *P. aeruginosa* biofilms grown on glass slide in solution of autoinducer according to comparative example 2.
Figure 20:
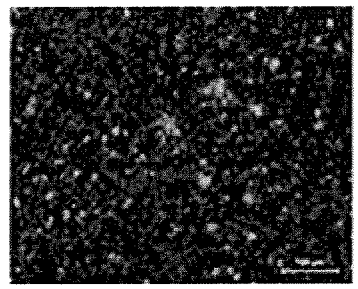
Figure 21:
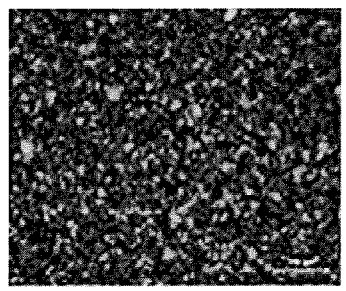

FIG. 13 showed a microscopic image depicting *P. aeruginosa* attached on the specimen in nutrient flask containing QS antagonist according to exemplary embodiment 1 of the present invention. FIG. 14 showed a microscopic image depicting *P. aeruginosa* attached on the specimen in nutrient flask containing distilled water according to comparative example 1. FIG. 15 showed a microscopic image depicting *P. aeruginosa* attached on the specimen in nutrient flask containing autoinducer according to the comparative example 2. FIGS. 16-18 showed microscopic images depicting *P. aeruginosa* attached on the specimens in nutrient flasks containing QS antagonists according to exemplary embodiment of the present invention. FIGS. 19-21 showed microscopic images depicting *P. aeruginosa* attached on the specimens in nutrient flasks containing autoinducer according to the comparative example 2.

As shown in FIGS. 13-21, the *P. aeruginosa* attached on specimen in the presence of QS antagonist according to the present invention was hardly observed. However, *P. aeruginosa* attached on specimen in the presence of distilled water or autoinducer was plentifully observed and initiated biofilm formation. Therefore, it was proven that the quorum sensing antagonist of this invention had the outstanding ability to prohibit biofilm formation.

The homoserine lactone derivatives according to the present invention have excellent efficacy as quorum sensing antagonists which inhibits cell-cell communications. The biofilm formation can be effectively prevented by blocking the gene expression of bacteria such as Gram-negative bacteria. Diseases can be also prevented by inhibiting the growth of bacteria. Especially, as the quorum sensing antagonist according to the present invention is designed to block the growth of bacteria by inhibiting the communication between bacteria, the propagation of bacteria can be prevented by using only the concentration of 1/100,000 of the conventional antibacterial agent to kill bacteria. Accordingly, the present invention can effectively be applied to home appliances or medical devices which require prevention of bacterial infection and biofilm formation.

While the disclosure has been shown and described with reference to certain preferred embodiments thereof, it will be understood by those skilled in the art that various changes in form and detail may be made therein without departing from the spirit and scope of the disclosure as defined by the appended claims.

What is claimed is:

1. A quorum-sensing antagonist comprising a molecular structure of the following formula:

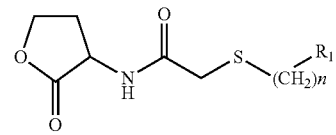

wherein n is an integer from 0 to 10, and wherein R1 indicates hydrogen, a carboxyl group, a nitrogen-containing hetero-aromatic hydrocarbon group, or a carboxyalkylthio group that has a carbon number from 1 to 10.

2. The quorum-sensing antagonist of claim 1, wherein the quorum-sensing antagonist further comprises molecular structures of the following formulas:

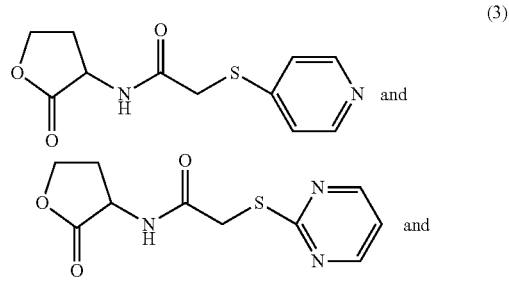

-continued

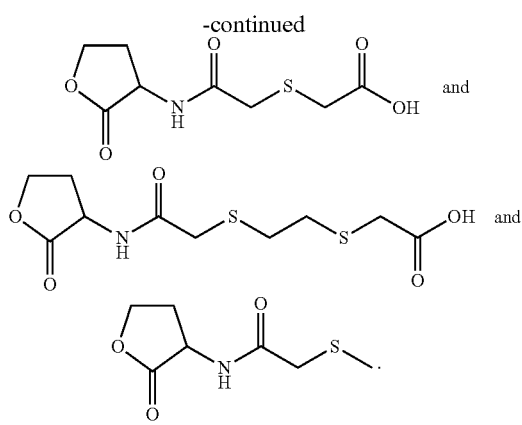

3. The quorum-sensing antagonist of claim 1, wherein the quorum-sensing antagonist further comprises a molecular structure of either of the following formulas:

4. The quorum-sensing antagonist of claim 1, wherein the quorum-sensing antagonist is configured to block quorum-sensing of Gram-negative bacteria.

5. The quorum-sensing antagonist of claim 1, wherein the quorum-sensing antagonist is configured to:
    contact an object; and
    inhibit biofilm formation on the object when the quorum-sensing antagonist contacts the object.

6. The quorum-sensing antagonist of claim 5, wherein the quorum-sensing antagonist further comprises a molecular structure of the following formula:

7. The quorum-sensing antagonist of claim 5, wherein the quorum-sensing antagonist is further configured to contact bacteria using acylhomoserine lactone as an autoinducer.

8. The quorum-sensing antagonist of claim 5, wherein the quorum-sensing antagonist is further configured to contact Gram-negative bacteria.

9. The quorum-sensing antagonist of claim 8, wherein the Gram-negative bacteria comprises at least *Vibrio harveyi, Agrobacterium tumefaciens, Pseudomonas aeruginosa, Escherichia coli, Aeronomas hydrophila, Burkholderia cepacia, Chromobacterium violaceum, Enterobacter agglomerans, Erwinia stewarti, Nitrosomas europea, Photobacterium fischeri, Pseudomonas aureofaciens, Rhizobium leguminosarum, Serratia liquefaciens*, or *Vibrio Fischeri.*

10. The quorum-sensing antagonist of claim 1, wherein the quorum-sensing antagonist is configured to contact an object.

11. The quorum-sensing antagonist of claim 10, wherein the quorum-sensing antagonist further comprises the molecular structure of the following formula:

12. The quorum-sensing antagonist of claim 10, wherein the quorum-sensing antagonist is contained in a solution and is further configured to contact the object via a spray method, a dipping method, or a brush method.

13. A quorum-sensing antagonist comprising a molecular structure of the following formula:

wherein n is an integer from 0 to 10, and
wherein R2 defines an aromatic hydrocarbon group or the carboxyalkylthio group.

14. The quorum-sensing antagonist of claim 13, wherein the quorum-sensing antagonist is configured to block quorum-sensing of Gram-negative bacteria.

15. The quorum-sensing antagonist of claim 13, wherein the quorum-sensing antagonist is configured to:
    contact an object; and
    inhibit biofilm formation on the object when the quorum-sensing antagonist contacts the object.

16. The quorum-sensing antagonist of claim 15, wherein the quorum-sensing antagonist is further configured to contact bacteria using acylhomoserine lactone as an autoinducer.

17. The quorum-sensing antagonist of claim 15, wherein the quorum-sensing antagonist is further configured to contact Gram-negative bacteria.

18. The quorum-sensing antagonist of claim 17, wherein the Gram-negative bacteria comprises at least *Vibrio harveyi, Agrobacterium tumefaciens, Pseudomonas aeruginosa, Escherichia coli, Aeronomas hydrophila, Burkholderia cepacia, Chromobacterium violaceum, Enterobacter agglomerans, Erwinia stewarti, Nitrosomas europea, Photobacterium fischeri, Pseudomonas aureofaciens, Rhizobium leguminosarum, Serratia liquefaciens*, or *Vibrio Fischeri.*

19. The quorum-sensing antagonist of claim 13, wherein the quorum-sensing antagonist is configured to contact an object.

20. The quorum-sensing antagonist of claim 19, wherein the quorum-sensing antagonist is contained in a solution and is further configured to contact the object via a spray method, a dipping method, or a brush method.

* * * * *